United States Patent

Kasap

Patent Number: 5,708,204
Date of Patent: Jan. 13, 1998

[54] FLUID FLOW RATE ANALYSIS METHOD FOR WIRELINE FORMATION TESTING TOOLS

[75] Inventor: Ekrem Kasap, Houston, Tex.

[73] Assignee: Western Atlas International, Inc., Houston, Tex.

[21] Appl. No.: 718,976

[22] Filed: Sep. 26, 1996

Related U.S. Application Data

[63] Continuation-in-part of Ser. No. 429,722, Apr. 27, 1995, Pat. No. 5,587,525, which is a continuation-in-part of Ser. No. 48,814, Apr. 16, 1993, Pat. No. 5,473,939, which is a continuation-in-part of Ser. No. 903,088, Jun. 19, 1992, abandoned.

[51] Int. Cl.$^6$ .................................................. E21B 49/00
[52] U.S. Cl. .................................. 73/152.52; 73/152.05
[58] Field of Search .......................... 73/152.51, 152.52, 73/152.54, 152.02, 152.05, 38

[56] References Cited

U.S. PATENT DOCUMENTS

| | | | |
|---|---|---|---|
| 3,332,483 | 7/1967 | Wyllie | 73/152.05 X |
| 3,771,360 | 11/1973 | Prats | 73/152.51 |
| 4,797,821 | 1/1989 | Petak et al. | 73/152.52 X |
| 4,799,157 | 1/1989 | Kucuk et al. | 73/152.05 X |
| 5,156,205 | 10/1992 | Prasad | 73/152.05 X |
| 5,335,542 | 8/1994 | Ramakrishnan et al. | 73/152.08 |
| 5,473,939 | 12/1995 | Leder et al. | 73/152.52 X |
| 5,602,334 | 2/1997 | Proett et al. | 73/152.05 |

FOREIGN PATENT DOCUMENTS

| | | | |
|---|---|---|---|
| 232-158-A | 1/1986 | Germany | 73/152.05 |
| 2161943 | 1/1986 | United Kingdom | 73/152.05 |

*Primary Examiner*—George M. Dombroske
*Assistant Examiner*—Paul D. Amrozowicz
*Attorney, Agent, or Firm*—Richard A. Fagin

[57] ABSTRACT

The invention is a method of determining the permeability of an earth formation using a wireline formation testing instrument. The method includes measuring pressure with respect to time at a probe in hydraulic communication with the earth formation, calculating time derivatives of the measured pressure, withdrawing fluid from the earth formation by increasing a volume of a chamber in hydraulic communication with the probe, measuring the volume of the chamber with respect to time, and calculating time derivatives of the measured volume. Increasing the volume of the chamber is stopped. The permeability is calculated when the measured pressure substantially stops increasing, by determining a slope of a linear relationship of the measured pressure with respect to a fluid flow rate calculated from the time derivative of the volume and the time derivative of the pressure.

22 Claims, 8 Drawing Sheets

FLUID FLOW RATE ANALYSIS METHOD FOR WIRELINE FORMATION TESTING TOOLS

CROSS REFERENCE TO RELATED APPLICATIONS

This is a continuation-in-part of patent application Ser. No. 08/429,722, now U.S. Pat. No. 5,587,525, filed on Apr. 27, 1995 and entitled, "Formation Fluid Flow Rate Determination Method and Apparatus for Electric Wireline Formation Testing Tools", which application is itself a continuation-in-part of patent application Ser. No. 08/048,814, now U.S. Pat. No. 5,473,939 filed on Apr. 16, 1993 and entitled, "Method and Apparatus for Pressure, Volume and Temperature Measurement and Characterization of Subsurface Formations", which is itself a continuation-in-part of patent application Ser. No. 07/903,088 filed on Jun. 19, 1992, now abandoned.

BACKGROUND OF THE INVENTION

1. Field of the Invention

The invention is related to the field of electric wireline instruments used to sample fluids contained in the pore spaces of earth formations. More specifically, the invention is related to methods of determining hydraulic properties of the earth formations by interpreting fluid pressure and flow rate measurements made by such instruments.

2. Description of the Related Art

Electric wireline formation testing instruments are used to withdraw samples of fluids contained within the pore spaces of earth formations and to make measurements of fluid pressures within the earth formations. Calculations made from these pressure measurements and measurements of the rate of flow of the fluids can be used to assist in estimating the total fluid content within a particular earth formation.

A typical electric wireline formation testing instrument is described, for example, in U.S. Pat. No. 5,377,755 issued to Michaels et at. Electric wireline formation testing instruments are typically lowered into a wellbore penetrating the earth formations at one end of an armored electrical cable. The formation testing instrument usually comprises a tubular probe which is extended from the instrument housing and then is impressed onto the wall of the wellbore. The probe is usually sealed on its outside diameter by an elastomeric seal or packing element to exclude fluids from within the wellbore itself from entering the interior of the probe, when fluids are withdrawn from the earth formation through the probe. The probe is selectively placed in hydraulic communication, by means of various valves, with sampling chambers included in the instrument. Hydraulic lines which connect the probe to the various sample chambers can include connection to a highly accurate pressure sensor to measure the fluid pressure within the hydraulic lines. Other sensors in the instrument can make measurements related to the volume of fluid which has entered some of the sample chambers during a test of a particular earth formation.

Properties of the earth formation which can be determined using measurements made by the wireline formation testing instrument include permeability of the formation and static reservoir pressure. Permeability is determined by, among other methods, calculating a rate at which a fluid having a known viscosity moves through the pore spaces within the formation when a predetermined differential pressure is applied to the formation. As previously stated, the formation testing instrument typically includes a sensor to make measurements related to the volume of fluid entering the sample chamber, and further includes a pressure sensor which can be used to determine the fluid pressure in the hydraulic lines connecting the probe to the sample chamber. It is further possible to determine the viscosity of the fluid in the earth formation by laboratory analysis of a sample of the fluid which is recovered from the sample chamber.

Methods known in the art for determining original reservoir pressure of the earth formations from pressure measurements made by electric wireline formation testing instruments are generally adapted from pressure transient analysis techniques such as the one described in A. F. Van Everdingen and W. Hurst, *The Application of the Laplace Transform to Flow Problems in Reservoirs*, Transactions of the AIME, vol. 186, p. 305, American Institute of Mining, Mechanical and Metallurgical Engineers, (1949). The method described in the Van Everdingen and Hurst reference includes causing a wellbore to flow for a predetermined period of time, stopping the flow (known as "shutting in" the wellbore) and measuring the buildup of formation pressure within the wellbore. The pressure measurements made over a period of time are extrapolated out to infinite time, so as to be able to estimate a static reservoir pressure. One simplifying assumption made in the analysis of pressure measurements by extrapolation is that the fluid flow through the earth formations is generally radially cylindrical. If the amount of time the earth formation is allowed to flow is sufficient prior to "shutting in" or terminating the flow to measure the buildup of pressure, this assumption is typically reasonable.

Electric wireline formation testing instruments more typically introduce flow in the earth formation that is hemispherical because of the limited size of the instrument probe with respect to the earth formation, and the very limited amount of time available for the system operator to allow the instrument to remain in place and withdraw fluid from the formation. This time limitation is related to the cost of the operation and to the increasing risk that the instrument will become stuck in the wellbore as the amount of time it remains in contact with the formation increases. Static reservoir pressures estimated using the cylindrical flow assumptions tend to be erroneous when the fluid flow is actually hemispherical.

Another drawback to the pressure measurement analysis techniques known in the art for electric wireline formation instruments, is they do not provide reliable means to estimate the formation permeability and the static reservoir pressure while a formation test is in progress. The methods known in the art require diagnostic tests to be applied to the pressure measurements after they are completed to determine whether the flow is hemispherical or cylindrical in nature. Consequently, there is no reliable means to determine a suitable time at which to terminate the pressure testing. It would be desirable to be able to determine such a termination time so as to minimize the amount of time the instrument is in contact with the earth formation, so as to minimize the operating cost and the risk of the instrument becoming stuck in the wellbore.

SUMMARY OF THE INVENTION

The invention is a method of determining the permeability of an earth formation using a wireline formation testing instrument. The method includes measuring the pressure, with respect to time, at a probe which is in hydraulic communication with the earth formation. Time derivatives of the measured pressure are calculated. Fluid is withdrawn from the earth formation by increasing the volume of a chamber in hydraulic communication with the probe. In a preferred embodiment, the chamber includes a pump having a measured displacement volume and hydraulic lines connecting the pump to the probe. The volume of the chamber is measured with respect to time, and time derivatives of the measured volume are calculated. Increasing the volume of the chamber is then stopped. Fluid continues to flow into the chamber while the pressure is measured. The permeability is calculated when the measured pressure substantially stops increasing. The permeability is calculated by determining the slope of a linear relationship of the measured pressure with respect to a formation fluid flow rate calculated from the time derivative of the volume and the time derivative of the pressure.

In the preferred embodiment, the relationship of a pressure function, corresponding to the measured pressure, is determined with respect to the value of the time derivative of the pressure. The slope of this relationship is related to the compressibility of fluid disposed in the chamber. The compressibility is used to refine the original calculation of the permeability by recalculation of the fluid flow rate from the time derivatives of the pressure and volume.

DESCRIPTION OF THE PREFERRED EMBODIMENT

Figure 1:
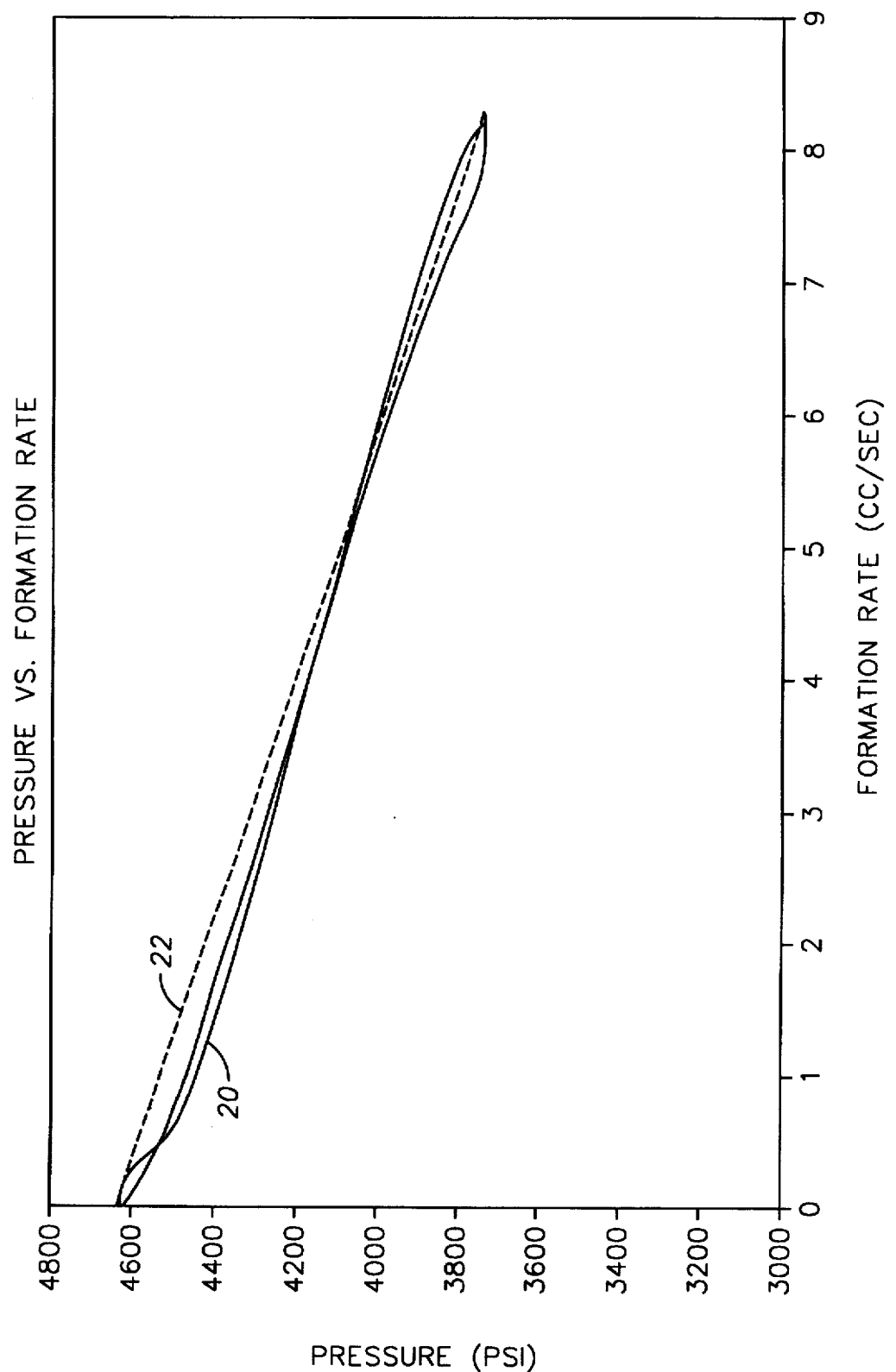
FIG. 1 shows a graph of measured pressure with respect to fluid flow rate in the earth formation.

An electric wireline formation testing instrument, suitable for making pressure and displaced fluid volume measurements as are used in the method of this invention, is described in U.S. Pat. No. 5,377,755 issued to Michaels et at, incorporated herein by reference. The instrument in the Michaels et al '755 patent is usually inserted into a wellbore at one end of an armored electrical cable. The instrument includes a probe adapted to be placed in hydraulic communication with the earth formation and sealed from the wellbore itself by a sealing element or "packer", and a pump selectively hydraulically connected to the probe so that the pump can withdraw fluids from the earth formation through the probe and selectively discharge the fluids into the wellbore or into a sample tank. The pump in the instrument includes a means for measuring the volume actually displaced by the pump during its operation, and a pressure sensor at the probe to measure the fluid pressure. The instrument includes means for transmitting pressure and pump volume measurements to the earth's surface for recording and analysis. It is to be understood that the instrument disclosed in the Michaels et al '755 patent is not the only type of formation testing instrument which could be used in the method of this invention. The essential features of a formation testing instrument as used in the method of this invention are a means for measuring the fluid pressure at the probe, and a means for measuring the total fluid volume in the instrument as the fluid is withdrawn from the earth formation through the probe. Both the pressure and the volume measurements must be referenced to the precise time at which each measurement is made.

It is to be explicitly understood that a formation testing instrument which is to be used in the method of the invention need not use a pump to withdraw fluid from the earth formation. For example, it is also possible to hydraulically connect the probe to a chamber having a lower internal pressure than the static pressure of the reservoir, so that fluid from the earth formation may flow through the probe into the chamber. It is only necessary that the total volume of the chamber and hydraulic lines connecting the probe to the chamber be known or precisely determinable. The pump disclosed in the Michaels et al '755 patent provides certain advantages in the method of the invention, not the least of which is that the volume of the pump is precisely determinable, and the rate of increase of the pump displacement volume is controllable so that change in phase of the fluid in the earth formation is minimized or eliminated during withdrawal of the fluid from the earth formation.

Analysis of the pressure and fluid volume measurements by the method of the invention assumes that the flow from earth formations into the probe is approximately hemispherical. In the method of the invention, an equation describing hemispherical flow has been modified to reflect the fact that the probe is sealed to the wall of the wellbore for only a small axial distance along the wellbore wall, and that the inner surface of the probe which is in contact with the earth formation is not itself hemispherical. The modified hemispherical flow equation describing the fluid flow into the probe from the earth formation is based on D'Arcy's law and can be expressed as:

$$q_f = \frac{k G_o r_i (P^* - P(t))}{\mu} \quad (1)$$

where $q_f$ in equation (1) represents the volumetric flow rate of fluids from the earth formation into the probe, $P^*$ represents the static reservoir (earth formation) fluid pressure, and $P(t)$ represents the pressure in the probe with respect to time t. $G_o$ is a dimensionless constant, referred to as the "geometric factor", which accounts for differences between "true" hemispherical flow and the actual system defined by the probe and its sealing element. $k$, $r_i$, and $\mu$ represent, respectively, the permeability of the earth formation, the effective radius of the probe, and the viscosity of the fluid flowing into the probe. The permeability and viscosity in the flow equation will be recognized by those skilled in the art as making up the "mobility" of the fluid in the earth formation.

The apparatus in the Michaels et al '755 patent measures the amount of volumetric displacement of its pump, rather than measuring the actual volumetric flow rate at the probe. During an intake stroke of the pump, fluid is withdrawn by the pump through the probe, but the fluid initially disposed in hydraulic lines connecting the probe to the pump inlet, as well as the fluid disposed in the pump itself, will be expanded to some extent as the pump creates a pressure drop. The amount of the expansion, as will be further explained, depends on the volume of fluid in the pump and the hydraulic lines, and on the compressibility of the fluid in the pump and the lines. Expansion of this fluid will cause some difference between the volumetric flow rate from the earth formation into the probe (which is the identified quantity "fluid flow rate" in equation (1)), and the volumetric displacement rate of the pump. The difference between the fluid flow rate and the volumetric displacement rate can be quantified as the "accumulation rate", $q_{ac}$, and can be calculated by the expression:

$$q_{ac} = q_{dd} - q_f \qquad (2)$$

where $q_{dd}$ represents the volumetric displacement rate of the pump, referred to as the "drawdown rate". The drawdown rate is calculated as the displaced pump volume per unit time. It may be calculated from the pump volume measurements as the time derivative of the volume, dV/dt. The drawdown rate, $q_{dd}$, must be known in order to perform the method of the invention, but it need not be constant during a fluid test.

The accumulation rate, $q_{ac}$, can be expressed in terms of the compressibility of the fluid disposed in the hydraulic lines and the pump ($C_{sys}$), and the total volume of the hydraulic lines and the pump ($V_{sys}$) by the expression:

$$-C_{sys}V_{sys}\frac{\partial P(t)}{\partial t} = q_{ac} \qquad (3)$$

where $\partial P(t)/\partial t$ represents the time derivative of the measured pressure. The expression in equation (3) for the accumulation rate, and the expression in equation (1) defining the volumetric flow rate of the formation can be substituted into equation (2) to generate the following expression:

$$-C_{sys}V_{sys}\frac{\partial P(t)}{\partial t} = q_{dd} - (P^* - P(t))\frac{kG_o r_i}{\mu} \qquad (4)$$

The expression in equation (4) can be rearranged to provide the following expression:

$$P(t) = P^* - \frac{\mu}{(kG_o r_i)}\left(C_{sys}V_{sys}\frac{\partial P(t)}{\partial t} + q_{dd}\right) \qquad (5)$$

In equation (5), the pressure at the probe (with respect to time) P(t), is measured by the pressure sensor in the instrument. The pump displacement volume is readily converted, as previously explained, into the drawdown rate $q_{dd}$, and the time derivative of the pressure measurement is easily calculated. The volume of fluid in the hydraulic lines and the pump, $V_{sys}$, can be determined from the design of the instrument and the displaced volume of the pump. The solutions generated by the method of the invention include estimates of the initial reservoir pressure, P*, the compressibility of the fluid in the hydraulic lines ($C_{sys}$) and the fluid mobility in the earth formation. The steps to obtain these solutions will now be explained.

The first step is to estimate the static reservoir pressure, P*. From equation (5), the formation fluid flow rate, $q_f$, can be calculated from the time derivative of the pressure and the drawdown rate, $q_{dd}$, by the expression:

$$q_f = C_{sys}V_{sys}\frac{\partial P(t)}{\partial t} + q_{dd} \qquad (6)$$

The pressure measured at the probe P(t), has typically a substantially linear relationship with respect to the formation flow rate, $q_f$. This linear relationship has a slope, m, which is directly related to the fluid mobility in the earth formation by the expression:

$$m = -\frac{\mu}{kG_o r_i} \qquad (7)$$

and the slope, m, is also related to the permeability of the earth formation, k, by the expression:

$$k = -\frac{\mu}{G_o r_i m} \qquad (8)$$

The pressure intercept of the function in equation (5) (at which the formation flow rate, $q_f$, is equal to zero) will occur substantially at the static reservoir pressure, P*. The relationship between measured pressure and formation flow rate can be observed in the graph in FIG. 1. The pressure and flow rate measurements are shown as individual points connected by a curve 20. A linear regression analysis of the points on curve 20 can be used to generate a line 22 for which the slope can be calculated. The slope of line 22 is related to the fluid mobility.

In order to use the relationship described in equation (6) to calculate the flow rate in the formation, $q_f$, it is necessary to make an initial estimate of the compressibility of the fluid disposed in the pump and the hydraulic lines ($C_{sys}$). Initial estimates can be obtained from the properties of a drilling fluid which is disposed in the wellbore during the drilling of the wellbore. These properties are typically well known, and can be extrapolated to the pressure and temperature extant in the wellbore at the depth at which the instrument is located to perform the test. It should be noted that the accuracy of the permeanbility calculated by equation (8) will be affected by the accuracy of the estimate of the compressibility. In the next step in the invention, the estimate of the compressibility can be improved. Equation (5) can be rewritten in the form:

$$P(t) + \frac{\mu q_{dd}}{kG_o r_i} = P^* - \frac{\mu C_{sys}V_{sys}}{kG_o r_i}\frac{\partial P(t)}{\partial t} \qquad (9)$$

A relationship of the value of the expression in the left hand side of equation (9) (referred to as the "pressure function") can be determined with respect to the time derivative of the pressure, $\partial P(t)/\partial t$. The relationship of the pressure function with respect to the time derivative of pressure is typically linear and has a slope, m, which can be determined by the expression:

$$m = -\frac{\mu C_{sys}V_{sys}}{kG_o r_i} \qquad (10)$$

The slope calculated by equation (10) can be used to determine an improved estimate of the compressibility by the expression:

$$C_{sys} = \frac{mkG_o r_i}{\mu V_{sys}} \qquad (11)$$

Figure 2:
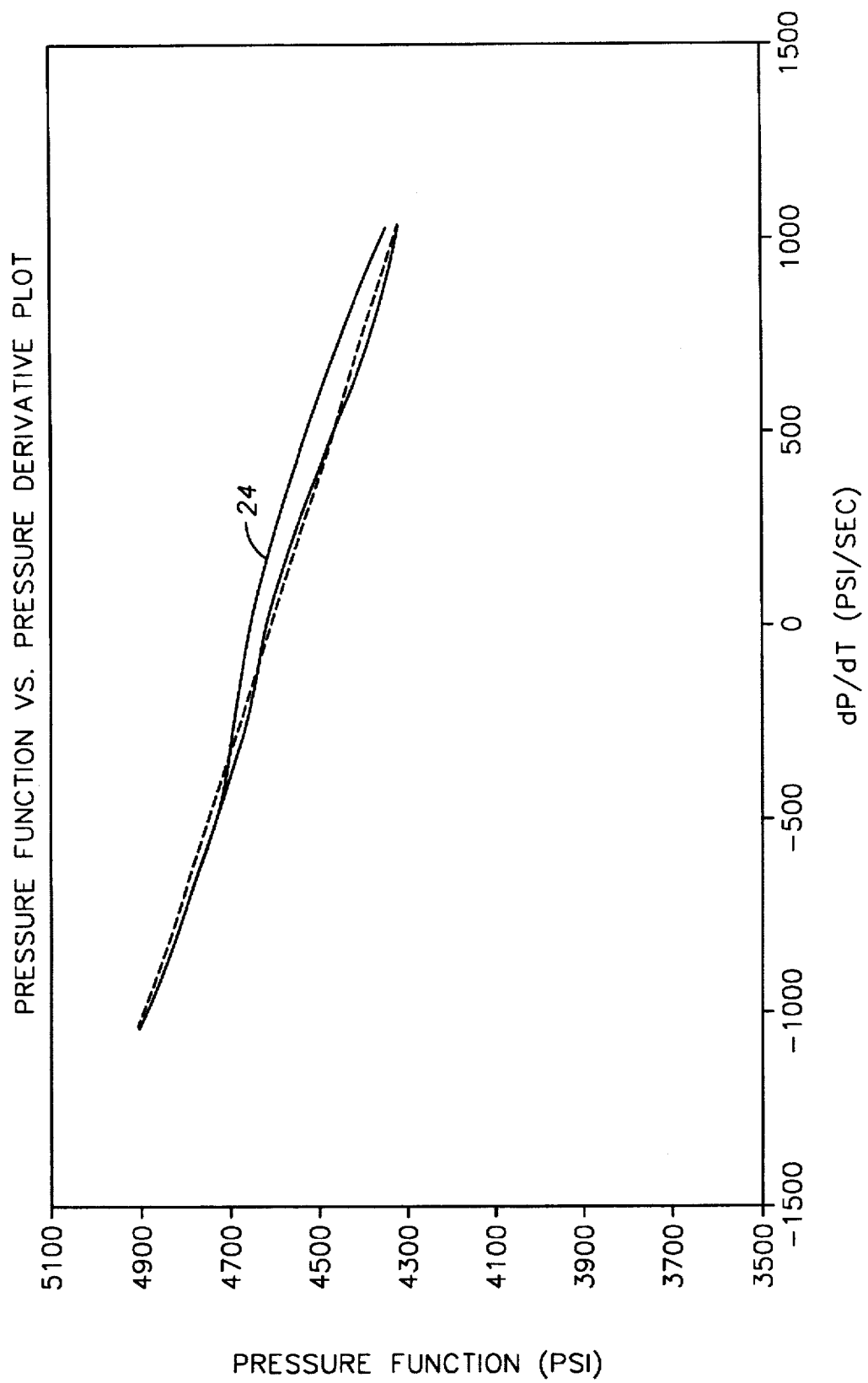
FIG. 2 shows a graph of measured pressure with respect to the time derivative of the measured pressure used to improve the estimate of fluid compressibility.

The relationship between the value of the expression of the left hand side of equation (9) with respect to the time derivative of the pressure is shown as a graph in FIG. 2. The value of the expression is shown plotted on the ordinate axis, and this value should equal the static reservoir pressure P* when the value of the time derivative of the pressure equals zero. The improved value of compressibility estimated using equation (11) can then be reentered into equation (5) to calculate an improved estimate of permeability of the earth formation.

Figure 3:
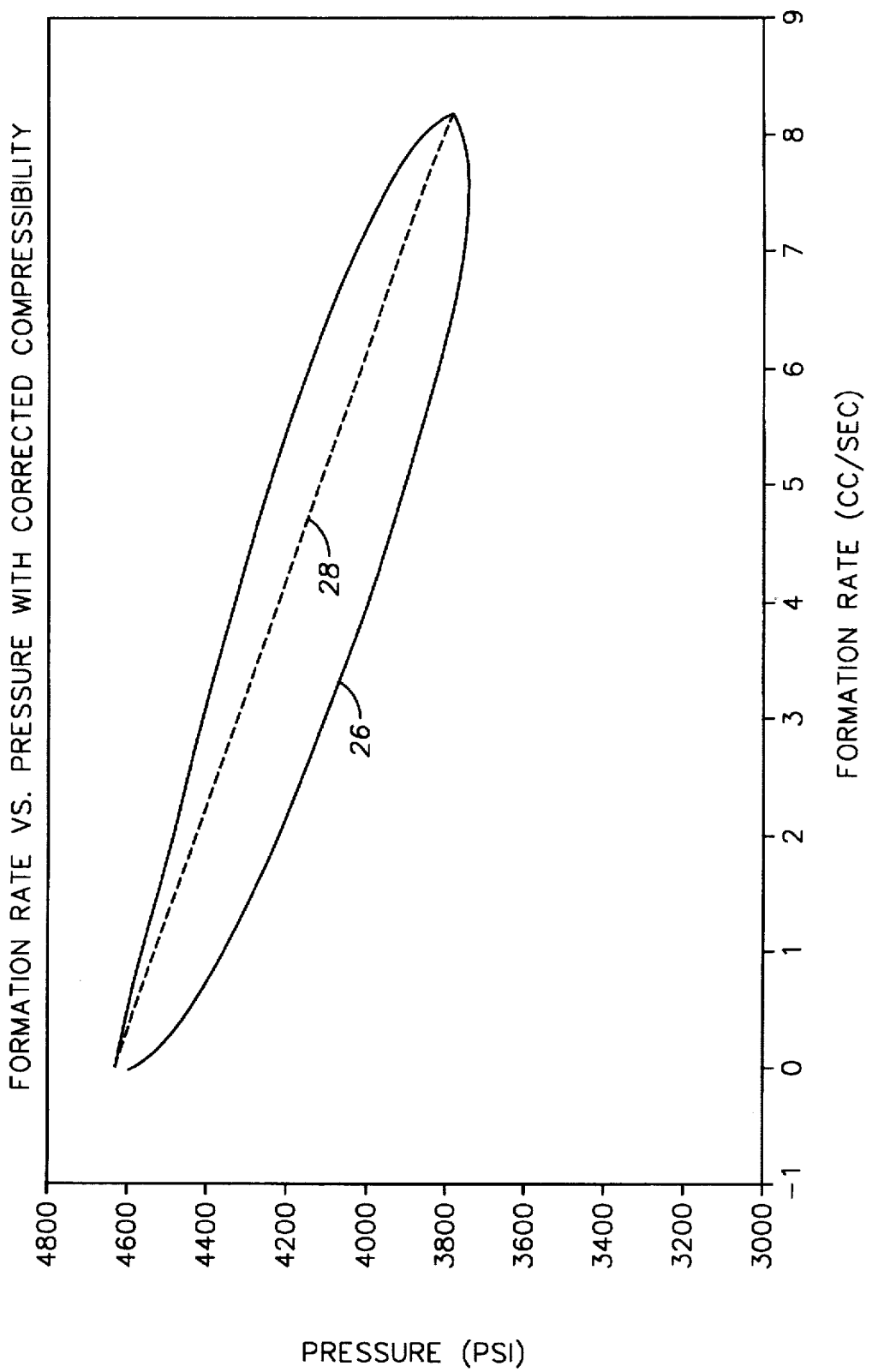
FIG. 3 shows a graph of measured pressure with respect to fluid flow rate after improvement of the estimate of fluid compressibility.

The relationship between formation flow rate and probe pressure using the improved estimate of compressibility is shown as a graph in FIG. 3. Curve 26 connects the individual points from pressure measurements compared with the values of formation flow rate calculated using the improved estimate of compressibility. Line 28 represents the best fit of the points and it has a slope corresponding to the formation permeability.

It is also possible to check the calculations of permeability and compressibility by comparing synthetic pressure calculations with the actual pressure measurements made by the formation testing instrument. The synthetic pressure calculations can be generated by using the estimated values of compressibility and permeability, and the calculated values of pressure derivative. Equation (5) represents a linear equation having two independent variables and three constants:

where the constants a, b and c are:

$$y(t) = ax_1 + bx_2 + c$$

$$y = P(t), x_1 = \frac{\partial P(t)}{\partial t}, x_2 = q_{dd} \qquad (12)$$

$$a = -\frac{C_{sys} V_{sys} \mu}{kG_o r_i}, b = -\frac{\mu}{kG_o r_i}, c = P^* \qquad (13)$$

Figure 4:
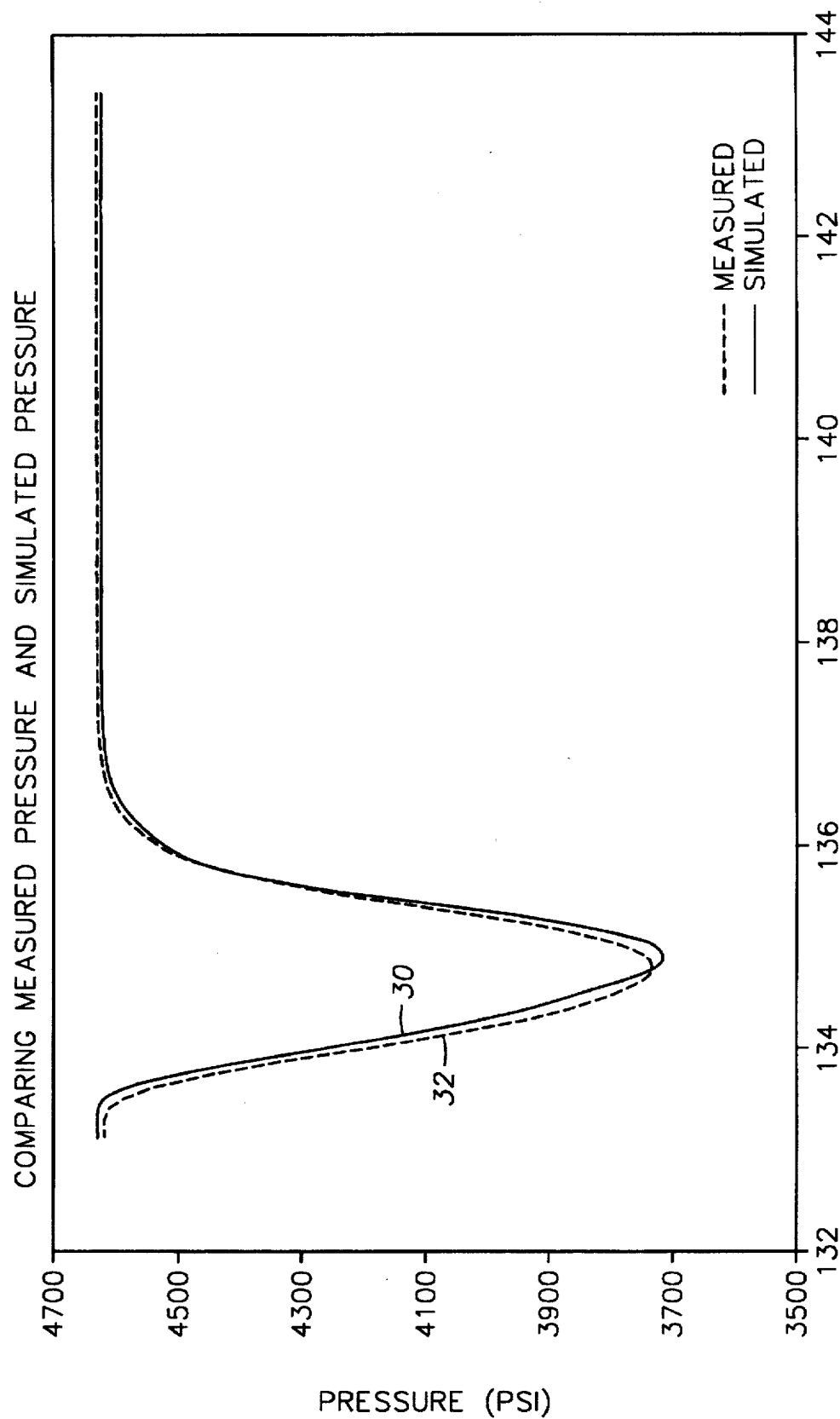
FIG. 4 shows a graph comparing synthetic pressure measurements to the actual fluid pressure measurements.

Multi variate linear regression can be used to calculate values of P(t) at each time for which a pressure measurement during a pressure test. The values of compressibility and permeability thus calculated can be checked by calculating the synthetic pressures. In the examples shown graphically in FIGS. 1, 2 and 3, synthetic pressure calculations are shown on a graph in FIG. 4 compared with the actual pressure measurements. The actual pressure measurements are shown as connected by curve 32, and the synthetic pressure calculations are shown as connected by curve 30. When there is substantial agreement between synthetic curve 32 and measured pressure curve 30, the values of permeability and compressibility are substantially correct.

DESCRIPTION OF ALTERNATIVE EMBODIMENTS

In the first embodiment of the invention, methods for calculating permeability of the earth formation, the static reservoir pressure, and the compressibility of the fluid in the instrument were explained. In some cases it may be desirable to make calculations of these parameters while a formation fluid test is in progress so that the amount of time that the instrument is in contact with the earth formation may be minimized. By making calculations during the test itself, the quality of the particular fluid test can be ascertained before the instrument is retracted from contact with the formation and moved to another position in the wellbore.

Equation (8), which is used to calculate formation permeability, can be rearranged to provide a calculation of the formation permeability for each individual measured pressure and volume:

$$k = \frac{\left(C_{sys} V_{sys} \frac{\partial P(t)}{\partial t} + q_{dd}\right)\mu}{(P^* - P(t)) r_i G_o} \qquad (14)$$

If equation (14) were used directly to calculate the permeability, any "noise" in the pressure and volume measurements would lead to discrepancies in the permeability calculations. It should also be apparent by reviewing the graph in FIG. 3 that on a point to point basis, there would be a different permeability calculated for the "drawdown" portion of a test and the "buildup portion of the test. The drawdown portion of the test is when the pump is increasing in volume, and the "buildup" portion of the test is when the pump has stopped increasing in volume and the measured pressure increases as fluids flow from the earth formation into the total volume defined by the hydraulic lines and the pump.

Figure 5:
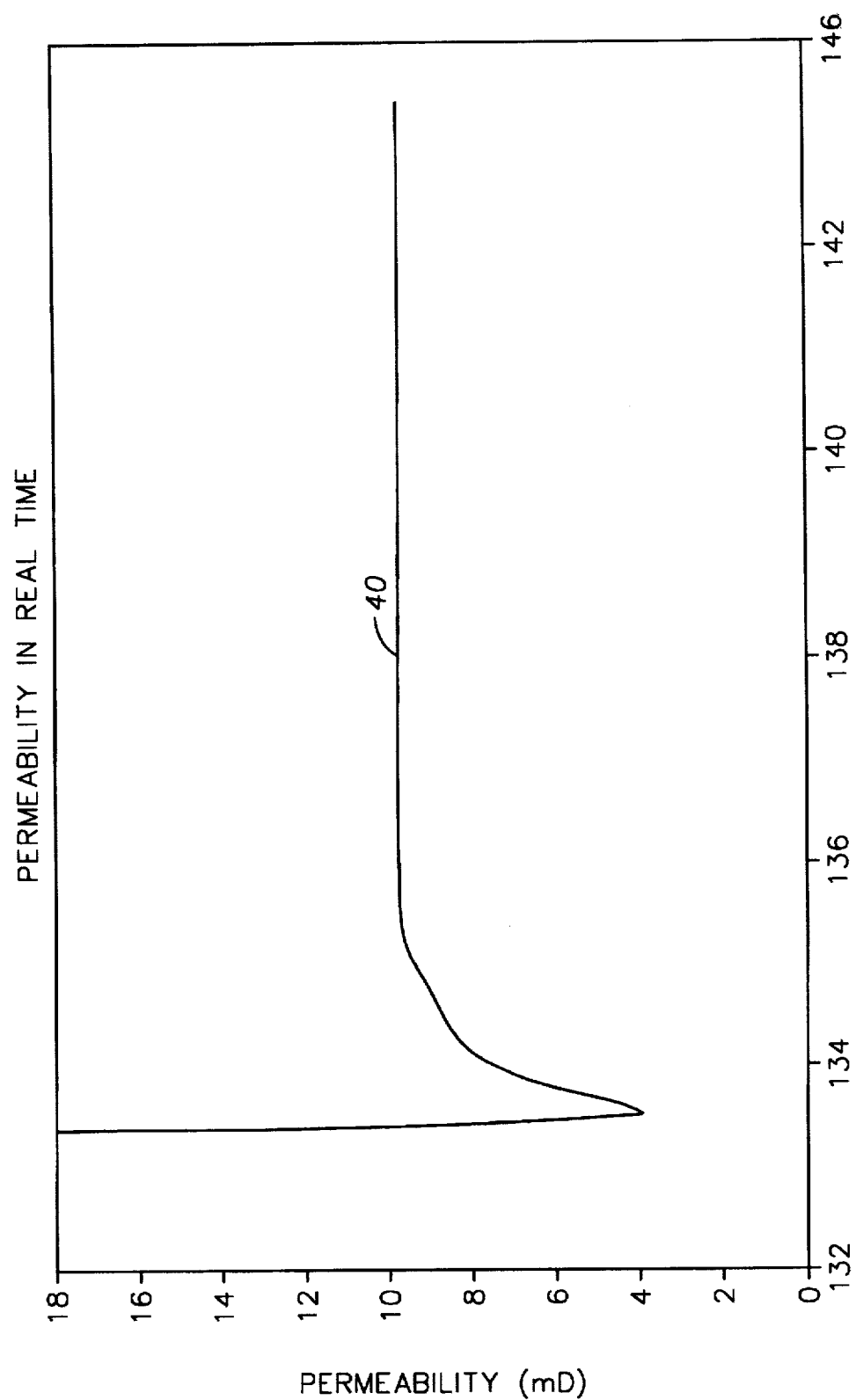
FIG. 5 shows a graph of an alternative method of calculating permeability which can be performed during a fluid test.

To improve the reliability of the calculation of permeability during a test, a weighted running average technique can be used. Equation (14) can be modified to calculate the weighted running average of each pressure measurement as shown in the expression:

$$k(t) = \frac{\mu}{r_i G_o} \frac{\sum_{j=1}^{n}\left(C_{sys} V_{sys} \frac{\partial P(t)}{\partial t} + q_{dd}\right)_j}{\sum_{j=1}^{n}(P^* - P(t))_j} \qquad (15)$$

where n represents the total number of pressure and volume data samples acquired up to time t. n would therefore increase as time t increases. A result of permeability calculation during testing is shown in the graph in FIG. 5. Curve 40, which connects the individual calculated values of permeability, shows rapid convergence to the final calculated value of permeability of about 10 millidarcies.

It is also possible to use the weighted running average technique to estimate compressibility during the test. Equation (8) can be rearranged to provide a calculation of the compressibility at each measured pressure and volume:

$$C_{sys} = \frac{kG_o r_i}{V_{sys} \mu} \frac{P^* - P(t) - \frac{\mu q_{dd}}{kG_o r_i}}{\frac{\partial P(t)}{\partial t}} \qquad (16)$$

and the weighted running average of the compressibility calculated for each measurement can be determined by the following expression:

$$C_{sys} = \frac{kG_o r_i}{V_{sys} \mu} \frac{\sum_{j=1}^{n}\left(P^* - P(t) - \frac{\mu q_{dd}}{kG_o r_i}\right)_j}{\sum_{j=1}^{n}\left(\frac{\partial P(t)}{\partial t}\right)_j} \qquad (17)$$

Figure 6:
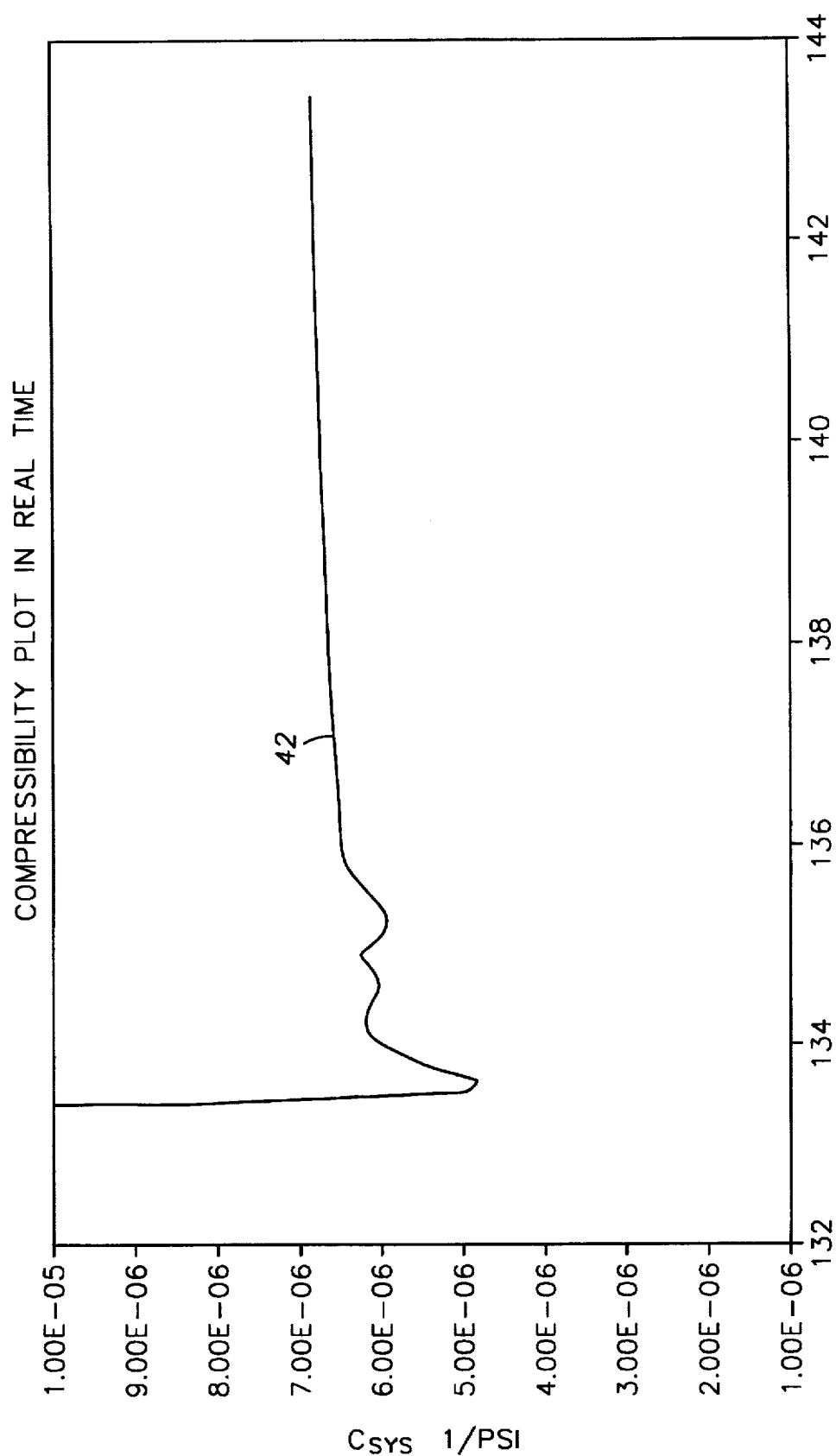
FIG. 6 shows a graph of an alternative method of calculating compressibility which can be performed during a fluid test.
Figure 7:
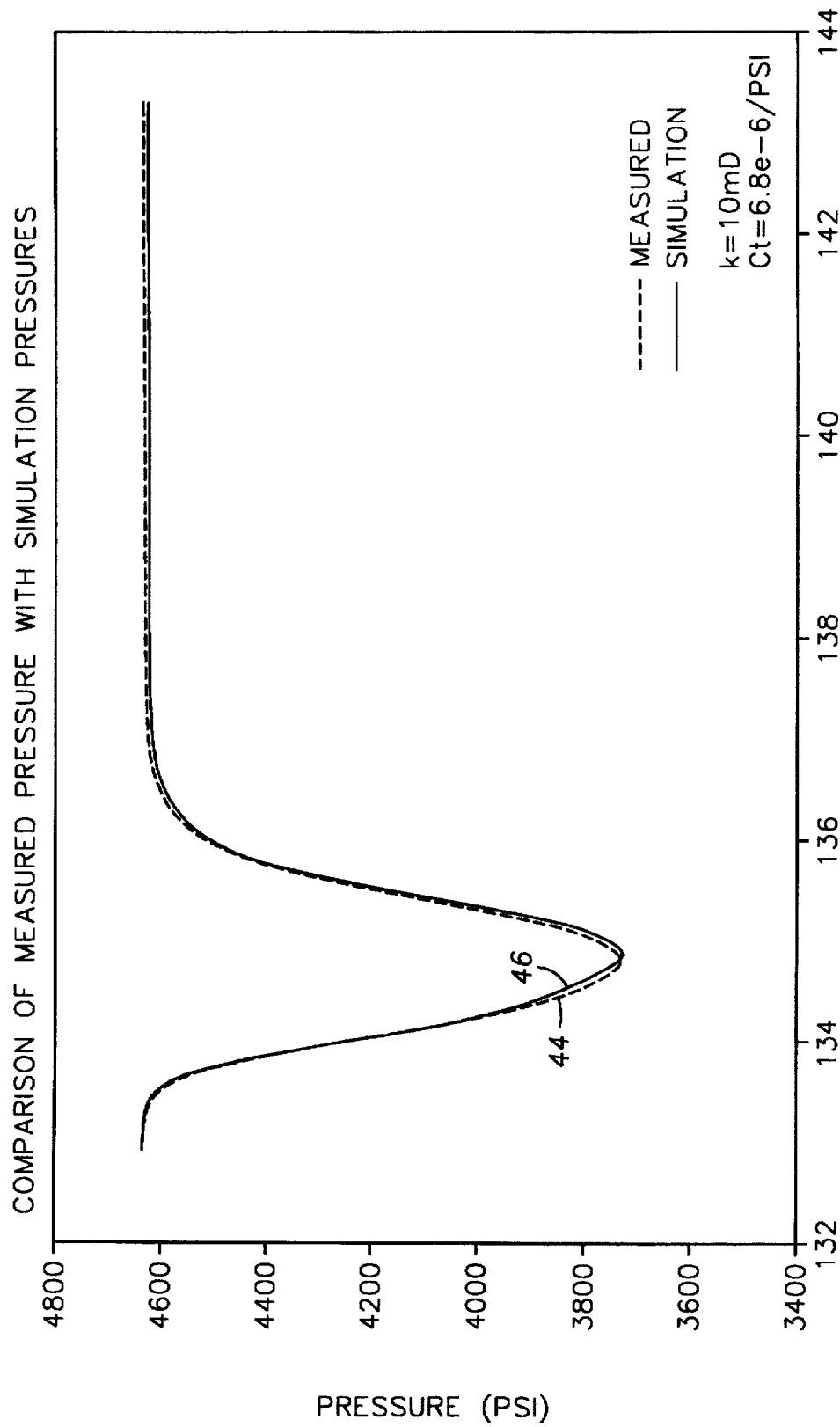
FIG. 7 shows a graph of synthesized pressure values based on permeability and compressibility calculated by the methods shown graphically in FIGS. 5 and 6, compared with measured pressure values from the instrument.

A graph of the resulting calculations of compressibility can be observed by referring to FIG. 6. Curve 42, which connects the individual calculations of compressibility, shows convergence at about $6.8 \times 10^{-6}$ psi$^{-1}$. To confirm the result of the permeability calculation and of the compressibility calculation, a numerical simulation of the pressure measurements can be made as described in A. Samaha et al, *Near Wellbore Permeability and Damage Measurements: Experiments and Numerical Simulations for Interpretation of WFT Data*, paper no. 35150, Society of Petroleum Engineers, Richardson, Tex. (1996). The results of such a simulation are shown in comparison to measured pressure data in the graph of FIG. 7. The measured pressures are connected by curve 44 and the simulated pressures are connected by curve 46. It can be concluded from the result in the graph of FIG. 7 that the calculated permeability and compressibility are substantially correct.

It is also possible to generate a reservoir pressure plot during the test which can provide a reliable indication of when the test should be ended. Equation (3) can be rearranged into the form:

$$P^* = P(t) + F \frac{\partial P(t)}{\partial t} \qquad (18)$$

Figure 8:
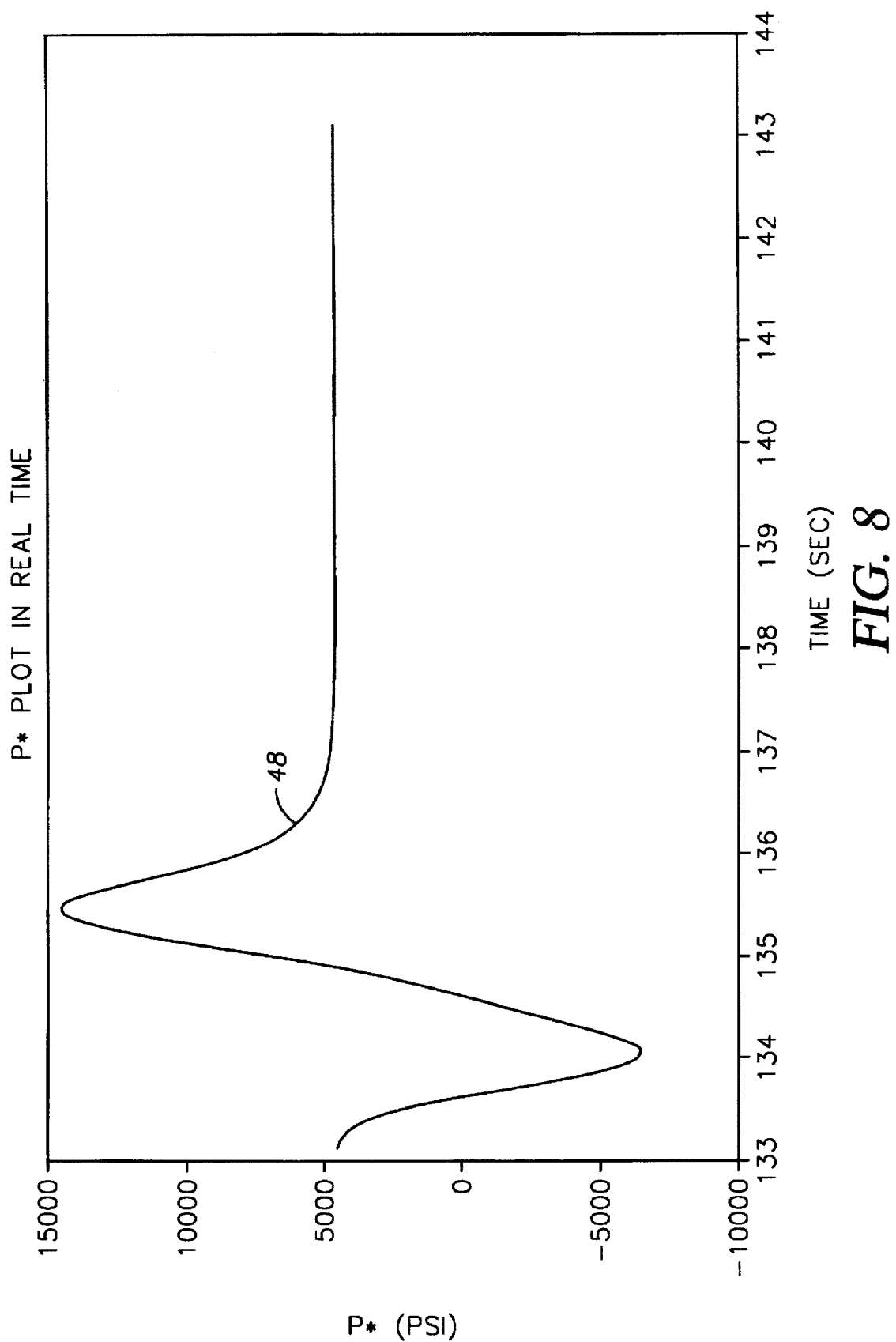
FIG. 8 shows a graph of an alternative method of calculating static reservoir pressure which can be performed during a fluid test.

At the end of the drawdown portion of the test (during the buildup portion), when the pump volume change is zero, the value of F will be a constant. Addition of the derivative term on the right hand side of equation (18) to the pressure measurements will have the effect of magnifying variations in pressure. The measured pressure will be approximately at the static reservoir pressure when the derivative term is approximately zero. To use the relationship in equation (18) it is not necessary to precisely calculate a value of F from an explicit solution to equation (3). It has been determined that a value of 10 can provide reliable indication of when to terminate a formation test when the permeability is as low as 0.25 millidarcies when using an instrument such as the one described in the Michaels et al '755 patent. The value of F will depend on such factor as the radius of the probe and the mobility of the fluid in the particular earth formation. An example of a reservoir pressure determination made using equation (18) is shown in the graph in FIG. 8. Curve 48, which connects individual calculations from equation (18) shows early convergence at the final value of P* of about 4630 psi. The difference between the measured pressure and the calculated value of P* should approach zero as the test is nearing a preferred termination time. At the preferred termination time, the buildup period has extended long enough to reliably estimate the value of P*, but is no longer than that, to reduce the possibility of the instrument becoming stuck in the wellbore.

Those skilled in the art will readily devise other embodiments of this invention which do not depart from the spirit of the invention as disclosed herein. Accordingly, the invention should be limited in scope only by the attached claims.

What is claimed is:

1. A method of determining permeability of an earth formation using a wireline formation testing instrument, comprising:

measuring pressure with respect to time at a probe in hydraulic communication with said earth formation;

withdrawing fluid from said earth formation by increasing a volume of a chamber in hydraulic communication with said probe and measuring said volume;

calculating time derivatives of said measured pressure and said measured volume;

stopping increasing said volume of said chamber; and calculating said permeability when said measured pressure substantially stops increasing by determining a slope of a linear relationship of said measured pressure with respect to a formation flow rate, said formation flow rate calculated from said time derivative of said volume, said time derivative of said pressure, and an initial estimate of compressibility of a fluid initially disposed in said probe and hydraulic lines connecting said probe to said chamber, said initial estimate obtained by extrapolating a known compressibility of a fluid in a wellbore to a wellbore pressure and temperature extant at said instrument.

2. The method as defined in claim 1 further comprising:

calculating compressibility of a fluid disposed in said chamber by determining a slope of a linear relationship of a pressure function with respect to said time derivative of said pressure; and recalculating said permeability using said calculated compressibility to correct said slope of said relationship of said measured pressure to said formation flow rate.

3. The method as defined in claim 1 further comprising determining a static fluid pressure in said earth formation by determining an intercept of said linear relationship between said pressure and said formation flow rate.

4. The method as defined in claim 3 further comprising calculating said static fluid pressure at each time at which said pressure is measured by adding a proportion of said time derivative of said pressure to the value of said measured pressure.

5. The method as defined in claim 4 further comprising determining a time at which to withdraw said probe from hydraulic communication with said earth formation by determining when a difference between said calculated static reservoir pressure and said measured pressure is substantially zero.

6. A method of determining permeability of an earth formation using a wireline formation testing instrument, comprising:

measuring pressure with respect to time at a probe in hydraulic communication with said earth formation;

withdrawing fluid from said earth formation by increasing a volume of a chamber in hydraulic communication with said probe and measuring said volume;

generating an initial estimate of compressibility of a fluid initially disposed in said probe and hydraulic lines connecting said probe to said chamber, said initial estimate obtained by extrapolating a known compressibility of a fluid in a wellbore to a wellbore pressure and temperature extant at said instrument;

calculating time derivatives of said measured pressure and said measured volume at each time at which said pressure and said volume are measured;

calculating an instantaneous permeability from said time derivatives at each said time at which said pressure and said volume are measured, and from said initial estimate of compressibility; and calculating said permeability by generating a weighted running average of said instantaneous permeabilities.

7. The method as defined in claim 6 further comprising calculating an instantaneous compressibility of a fluid in said chamber for each time at which said pressure and said volume are measured, and calculating a compressibility of said fluid by generating a weighted running average of said instantaneous compressibilities.

8. A method of determining fluid flow properties of an earth formation penetrated by a wellbore using a wireline formation testing instrument, comprising:

inserting said testing instrument into said wellbore;

placing a fluid test probe in hydraulic communication with said formation, said probe hydraulically isolated from said wellbore;

withdrawing fluid from said earth formation into a chamber by increasing a volume of said chamber, while measuring a pressure of said fluid at said probe with respect to time and measuring said volume of said chamber with respect to time;

stopping withdrawal of said fluid by stopping increasing said volume while continuing to measure said pressure;

calculating time derivatives of said volume and time derivatives of said pressure;

determining a permeability of said earth formation by determining a slope of a linear relationship of said measured pressure with respect to a formation flow rate, said formation flow rate calculated from said time derivative of said volume, said time derivative of said pressure, and an initial estimate of compressibility of a fluid initially disposed in said probe and hydraulic lines connecting said probe to said chamber, said initial estimate obtained by extrapolating a known compressibility of a fluid in a wellbore to a wellbore pressure and temperature extant at said instrument.

9. The method as defined in claim 8 further comprising:
calculating a compressibility of a fluid disposed in said chamber by determining a slope of a linear relationship of a pressure function with respect to said time derivative of said pressure; and
redetermining said permeability using said calculated compressibility to correct said slope of said relationship of said measured pressure with respect to said fluid flow rate.

10. The method as defined in claim 8 further comprising determining a static fluid pressure in said earth formation by determining an intercept of said linear relationship between said pressure and said flow rate.

11. The method as defined in claim 10 further comprising calculating said static fluid pressure at each time at which said pressure is measured by adding a proportion of said time derivative of said pressure to said measured pressure.

12. The method as defined in claim 11 further comprising determining a time at which to withdraw said probe from hydraulic communication with said earth formation by determining when a difference between said static reservoir pressure and said measured pressure is substantially zero.

13. The method as defined in claim 12 further comprising calculating said permeability for each time at which said pressure and said volume are measured, wherein said permeability is calculated by a weighted running average.

14. The method as defined in claim 13 further comprising comparing said permeability calculated from said weighted running average with said permeability calculated from said slope of said linear relationship, thereby determining a time at which said probe should be withdrawn from hydraulic communication with said earth formation.

15. The method as defined in claim 14 further comprising calculating said compressibility for each time at which said pressure and said volume are measured, wherein said compressibility is calculated by a weighted running average.

16. The method as defined in claim 15 further comprising comparing said compressibility calculated from said weighted running average with said compressibility calculated from said slope of said linear relationship, thereby determining a time at which said probe should be withdrawn from hydraulic communication with said earth formation.

17. A method of determining fluid flow properties of an earth formation penetrated by a wellbore using a wireline formation testing instrument, comprising:
inserting said testing instrument into said wellbore;
placing a fluid test probe in hydraulic communication with said formation, said probe hydraulically isolated from said wellbore;
withdrawing fluid from said earth formation into a chamber by increasing a volume of said chamber, while measuring a pressure with respect to time of said fluid at said probe and measuring said volume of said chamber with respect to time;
stopping withdrawal of said fluid by stopping increasing said volume while continuing to measure said pressure;
calculating time derivatives of said volume and time derivatives of said pressure;
determining a static pressure of said earth formation by determining an intercept of a linear relationship of said measured pressure with respect to a fluid flow rate, said fluid flow rate calculated from said time derivative of said volume, said time derivative of said pressure, and an initial estimate of compressibility of a fluid initially disposed in said probe and hydraulic lines connecting said probe to said chamber, said initial estimate obtained by extrapolating a known compressibility of a fluid in a wellbore to a wellbore pressure and temperature extant at said instrument.

18. The method as defined in claim 17 further comprising determining a compressibility of a fluid disposed in said chamber by determining a slope of a linear relationship of a pressure function with respect to said time derivative of said pressure.

19. The method as defined in claim 17 further comprising calculating said static fluid pressure at each time at which said pressure is measured by adding a proportion of said time derivative of said pressure to said measured pressure.

20. The method as defined in claim 19 further comprising determining a time at which to withdraw said probe from hydraulic communication with said earth formation by determining that a difference between said static reservoir pressure and said measured pressure is substantially zero.

21. A method of determining permeability of an earth formation using a wireline formation testing instrument, comprising:
measuring pressure with respect to time at a probe in hydraulic communication with said earth formation;
withdrawing fluid from said earth formation by increasing a volume of a chamber in hydraulic communication with said probe and measuring said volume;
calculating time derivatives of said measured pressure and said measured volume; stopping increasing said volume of said chamber;
calculating said permeability when said measured pressure substantially stops increasing by determining a slope of a linear relationship of said measured pressure with respect to a formation flow rate, said formation flow rate calculated from said time derivative of said volume, said time derivative of said pressure, and an initial estimate of compressibility of a fluid initially disposed in said probe and hydraulic lines connecting said probe to said chamber, said initial estimate obtained by extrapolating a known compressibility of a fluid in a wellbore to a wellbore pressure and temperature extant at said instrument;
calculating an instantaneous permeability from said time derivatives at each time at which said pressure and said volume are measured;
recalculating said permeability by generating a weighted running average of said instantaneous permeabilities; and
comparing said permeability recalculated by generating said weighted running average with said permeability calculated by determining said slope of said linear relationship.

22. The method as defined in claim 21 further comprising:
determining compressibility of a fluid disposed in said chamber by determining a slope of a linear relationship of a pressure function with respect to said time derivative of said pressure;
calculating an instantaneous compressibility of said fluid at each said time at which said pressure and said volume are measured;
recalculating said compressibility by generating a weighted running average of said instantaneous compressibilities; and
comparing said compressibility determined from said slope of said linear relationship with said recalculated compressibility.

* * * * *